(12) United States Patent
Parihar et al.

(10) Patent No.: US 8,414,596 B2
(45) Date of Patent: Apr. 9, 2013

(54) TISSUE RETRIEVAL DEVICE WITH GUSSETED POUCH

(75) Inventors: Shailendra K. Parihar, Mason, OH (US); Atul M. Godbole, Liberty Township, OH (US); Kevin A. Larson, South Lebanon, OH (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 402 days.

(21) Appl. No.: 12/693,485

(22) Filed: Jan. 26, 2010

(65) Prior Publication Data
US 2011/0184434 A1 Jul. 28, 2011

(51) Int. Cl.
*A61B 17/22* (2006.01)
(52) U.S. Cl. .......................................... 606/127
(58) Field of Classification Search .................. 600/184; 606/110, 113, 114, 115, 127, 128
See application file for complete search history.

(56) References Cited

U.S. PATENT DOCUMENTS

| 5,190,555 A | 3/1993 | Wetter et al. |
| 5,215,521 A | 6/1993 | Cochran et al. |
| 5,320,627 A | 6/1994 | Sorensen et al. |
| 5,337,754 A | 8/1994 | Heaven et al. |
| 5,370,647 A | 12/1994 | Graber et al. |
| 5,465,731 A | 11/1995 | Bell et al. |
| 5,480,404 A | 1/1996 | Kammerer et al. |
| 5,524,633 A | 6/1996 | Heaven et al. |
| 5,647,372 A | 7/1997 | Tovey et al. |
| 5,649,902 A | 7/1997 | Yoon |
| 5,735,289 A * | 4/1998 | Pfeffer et al. ............... 600/564 |
| 5,769,794 A | 6/1998 | Conlan et al. |
| 5,779,716 A | 7/1998 | Cano et al. |
| 5,836,953 A | 11/1998 | Yoon |

(Continued)

FOREIGN PATENT DOCUMENTS

| DE | 92 18 154 | 9/1993 |
| DE | 10 2008 019497 | 10/2009 |

(Continued)

OTHER PUBLICATIONS

International Search Report dated Apr. 4, 2011 for Application No. PCT/US2011/021817.

(Continued)

*Primary Examiner* — Ryan Severson
*Assistant Examiner* — Jonathan W Miles
(74) *Attorney, Agent, or Firm* — Frost Brown Todd LLC

(57) ABSTRACT

A tissue retrieval device includes an introducer tube and a tissue retrieval bag. The introducer tube is insertable into a patient through a trocar. The bag may be selectively exposed at the distal end of the introducer tube, receive a tissue specimen, and be withdrawn from the patient. The bag includes a plurality of folds allowing the bag to transition from a folded configuration to an unfolded configuration. The folds may extend along a length of the bag transverse to the introducer tube; or along a length of the bag parallel to the introducer tube. The folds may extend about a perimeter of the bag, such as a circumference of the bag, and may be spaced apart along a length of the bag transverse to the introducer tube. The folds may be formed by petals that provide the bag with a generally spherical configuration when the bag is unfolded.

15 Claims, 12 Drawing Sheets

U.S. PATENT DOCUMENTS

| | | |
|---|---|---|
| 5,971,995 A | 10/1999 | Rousseau |
| 6,409,733 B1 | 6/2002 | Conlon et al. |
| 6,673,080 B2 | 1/2004 | Reynolds et al. |
| 7,691,111 B2 | 4/2010 | Bates et al. |
| 7,762,959 B2 | 7/2010 | Bilsbury |
| 8,016,771 B2 | 9/2011 | Orban, III |
| 2004/0138587 A1 | 7/2004 | Lyons, IV |
| 2005/0267492 A1 | 12/2005 | Poncet et al. |
| 2006/0200170 A1 | 9/2006 | Aranyi |
| 2006/0247663 A1 | 11/2006 | Schwartz et al. |
| 2007/0088370 A1 | 4/2007 | Kahle et al. |
| 2011/0184311 A1 | 7/2011 | Parihar et al. |
| 2011/0184430 A1 | 7/2011 | Parihar et al. |
| 2011/0184431 A1 | 7/2011 | Parihar et al. |
| 2011/0184432 A1 | 7/2011 | Parihar et al. |
| 2011/0184433 A1 | 7/2011 | Parihar et al. |
| 2011/0184435 A1 | 7/2011 | Parihar et al. |
| 2011/0184436 A1 | 7/2011 | Shelton, IV et al. |

FOREIGN PATENT DOCUMENTS

| | | |
|---|---|---|
| EP | 0 578 997 | 1/1994 |
| EP | 0 950 376 | 10/1999 |
| WO | WO 93/15671 | 8/1993 |
| WO | WO 95/09666 | 4/1995 |
| WO | WO 98/38920 | 9/1998 |
| WO | WO 01/10308 | 2/2001 |
| WO | WO 2005/112783 | 12/2005 |

OTHER PUBLICATIONS

International Search Report dated Apr. 19, 2011 for Application No. PCT/US2011/021046.

International Search Report and Written Opinion dated Aug. 1, 2011 for Application No. PCT/US2011/021042.

International Search Report dated Oct. 11, 2011 for Application No. PCT/US2011/021049.

* cited by examiner

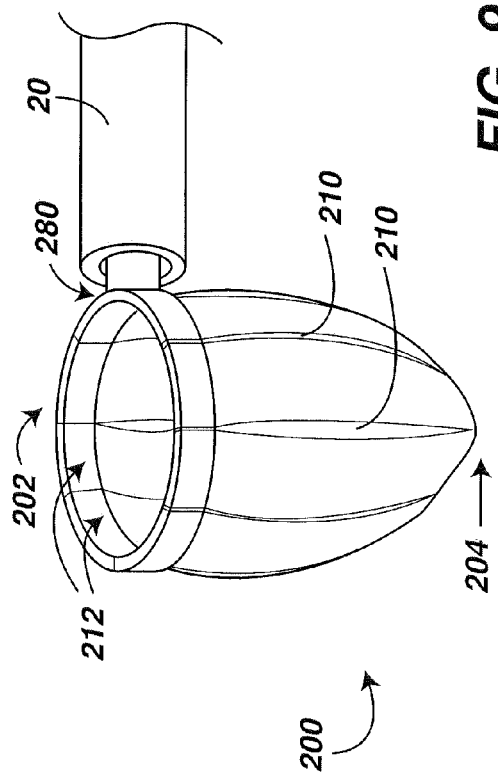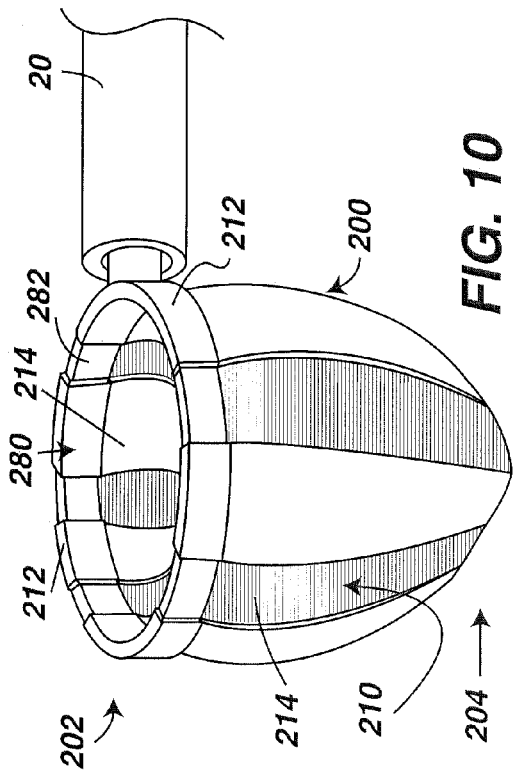

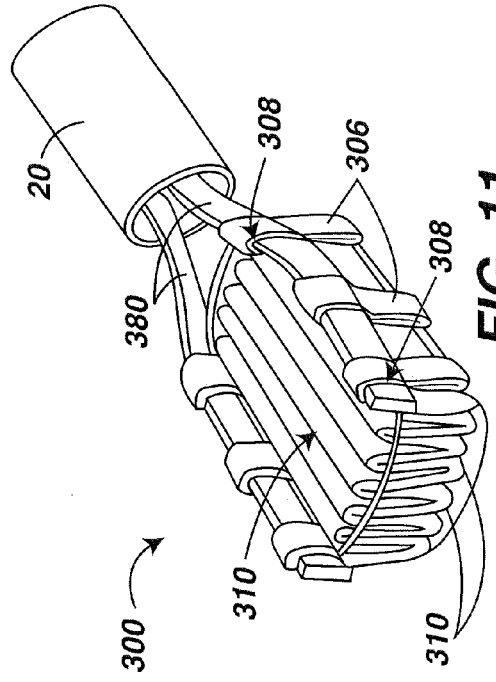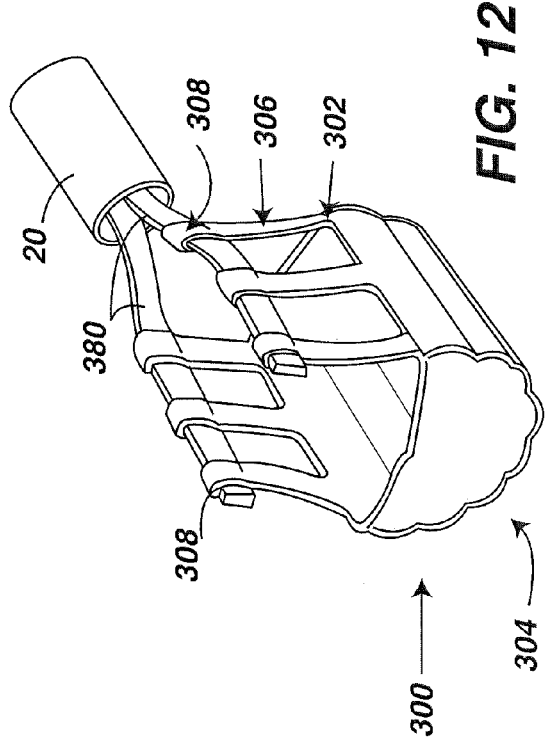

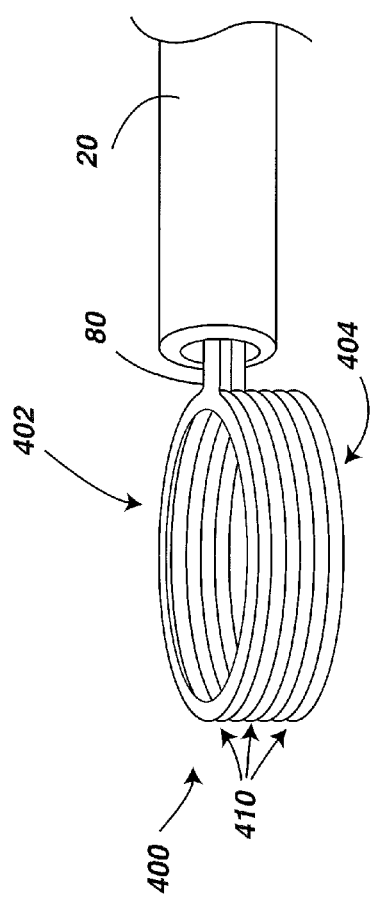
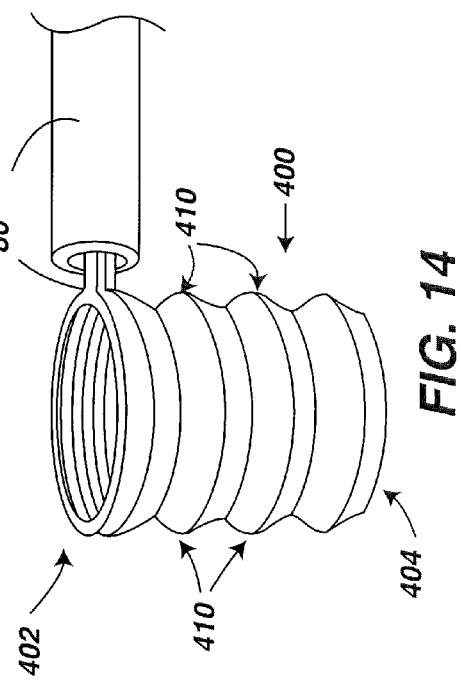

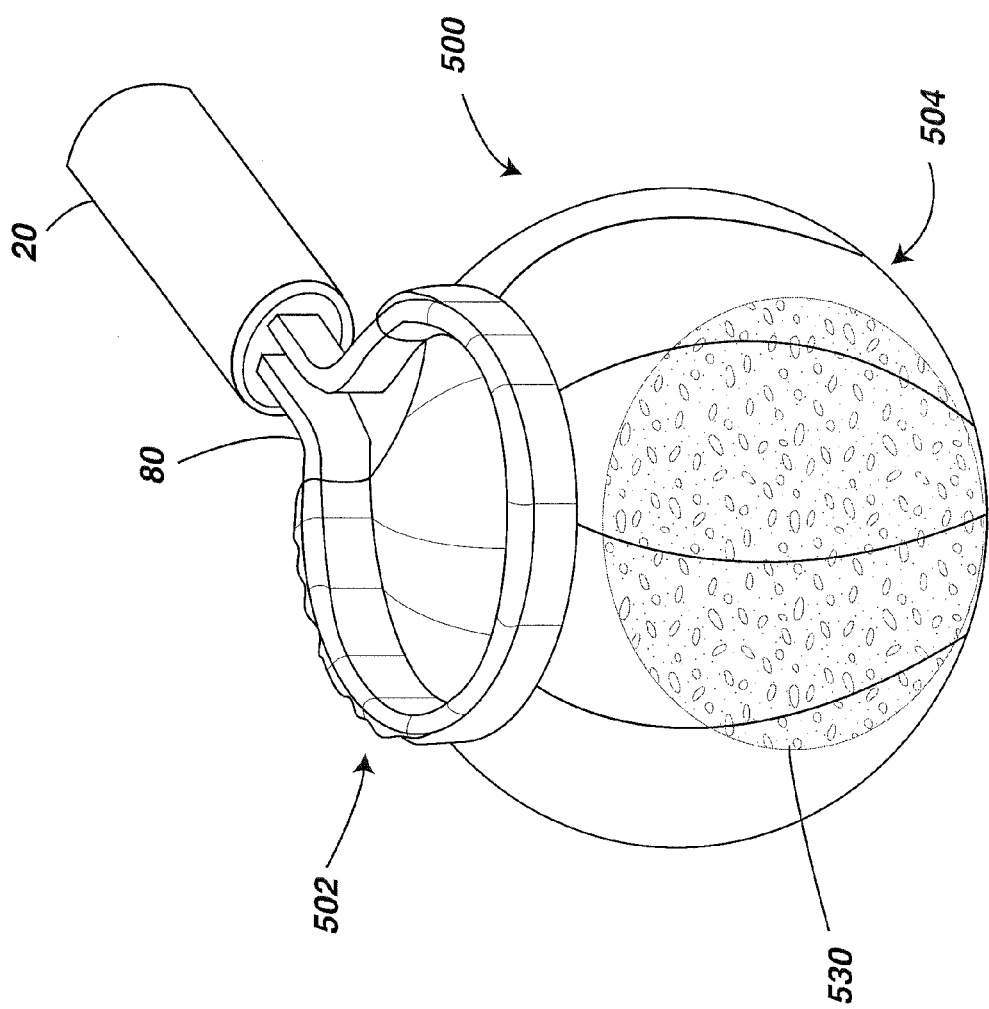

TISSUE RETRIEVAL DEVICE WITH GUSSETED POUCH

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal cavity. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 9 is a perspective view of another exemplary alternative retrieval bag, in a deployed position and in an un-expanded configuration.

FIG. 10 is a perspective view of the retrieval bag of FIG. 9, in the deployed position and in an expanded configuration.

FIG. 11 is a perspective view of another exemplary alternative retrieval bag, in a deployed position and in an un-expanded configuration.

FIG. 12 is a perspective view of the retrieval bag of FIG. 11, in the deployed position and in an expanded configuration.

FIG. 13 is a perspective view of another exemplary alternative retrieval bag, in a deployed position and in an un-expanded configuration.

FIG. 14 is a perspective view of the retrieval bag of FIG. 13, in the deployed position and in an expanded configuration.

FIG. 17 is a perspective view of the retrieval bag of FIG. 15, in the fully deployed position and in a fully expanded configuration.

Figure 1:
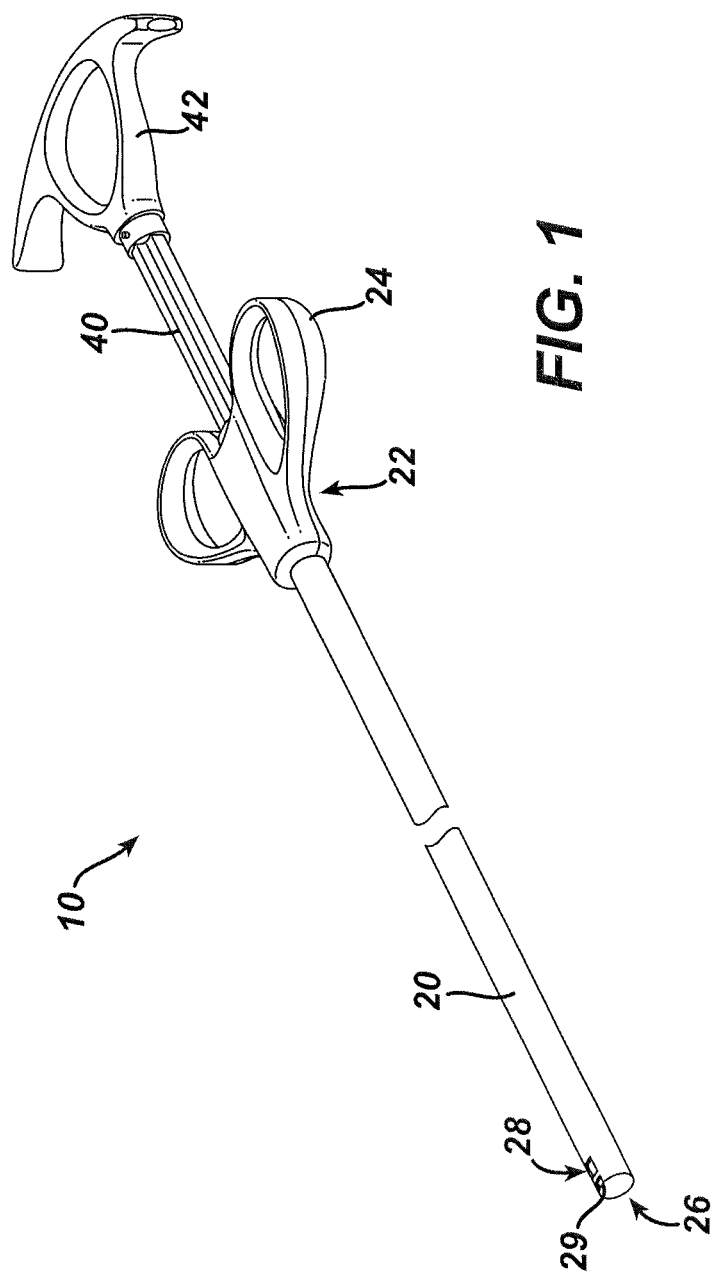
FIG. 1 is a perspective view of an exemplary tissue retrieval device, with a retrieval bag in a retracted position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Figure 2:
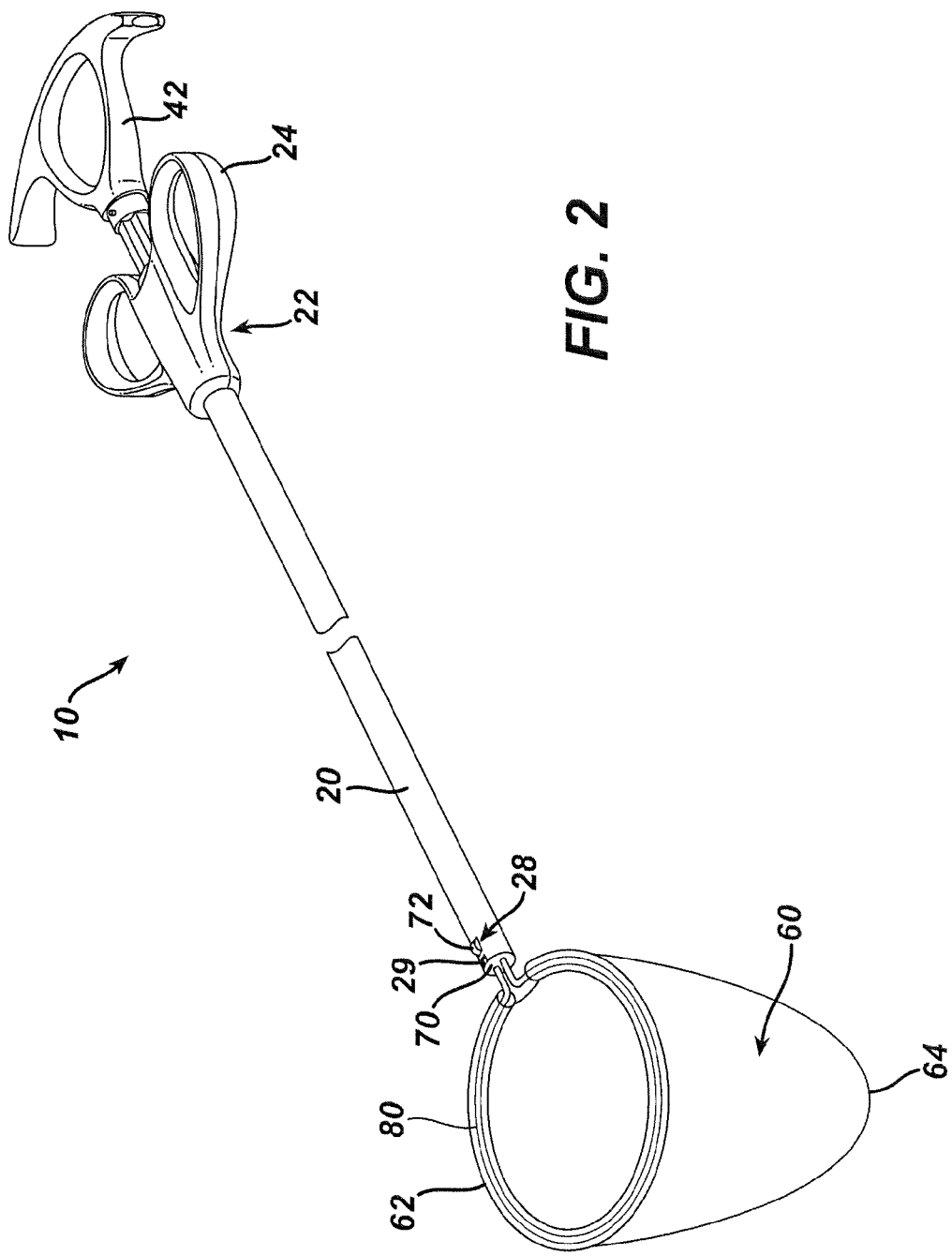
FIG. 2 is a perspective view of the tissue retrieval device of FIG. 1, with the retrieval bag in a deployed position.
Figure 3:
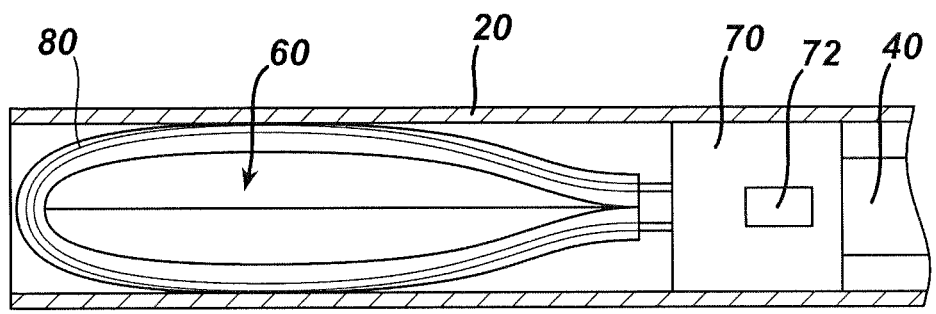
FIG. 3 is a partial top view of the tissue retrieval device of FIG. 1, with the retrieval bag in the retracted position and with the introducer tube shown in cross section.
Figure 4:
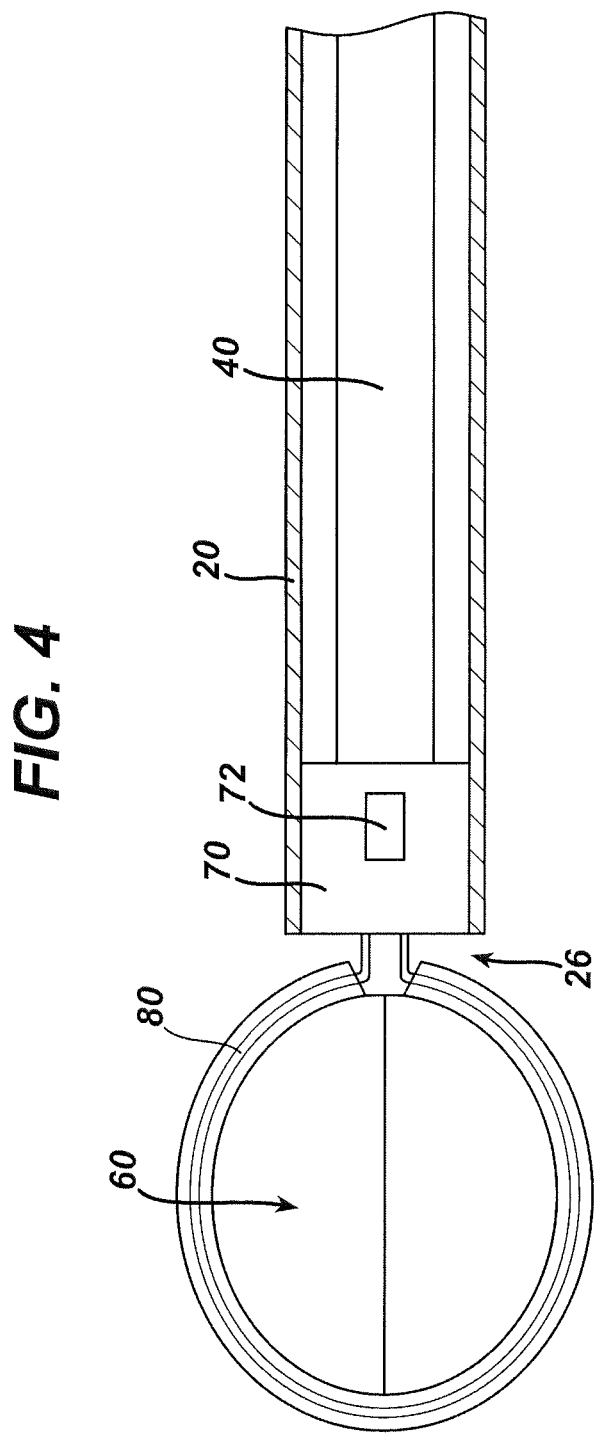
FIG. 4 is a partial top view of the tissue retrieval device of FIG. 1, with the retrieval bag in the deployed position and with the introducer tube shown in cross section.

FIGS. 1-4 show an exemplary tissue retrieval device (10). In this example, tissue retrieval device (10) comprises an elongate introducer tube (20), a handle (22) secured to the proximal end of introducer tube (20), an actuating rod (40), and a thumb ring (42) secured to the proximal end of actuating rod (40). Handle (22) comprises a pair of finger grips (24). As will be described in greater detail below, actuating rod (40) is slidable within the hollow interior of introducer tube (20) to selectively deploy a tissue retrieval bag (60) from introducer tube (20). In particular, with actuating rod (40) in a proximal position as shown in FIGS. 1 and 3, a user may insert their thumb in thumb ring (42), and insert their index and middle fingers in finger grips (24), then advance thumb ring (42) distally toward finger grips (24) to translate actuating rod (40) distally to a distal position as shown in FIGS. 2 and 4.

In the present example introducer tube (20) is formed of metal; while handle (22), actuating rod (40), and thumb ring (42) are formed of plastic. However, it should be understood that any suitable material or combination of materials may be used to form these components and other components described herein. Introducer tube (20) has an open distal end (26) and a side aperture (28) just proximal to open distal end (26). Introducer tube (20) of the present example is sized such that introducer tube (20) may be introduced to a surgical site through a trocar or other type of device. By way of example only, the outer diameter of introducer tube (20) may be approximately 5 mm (inclusive) and approximately 15 mm (inclusive) (e.g., approximately 10 mm, etc.). Alternatively, introducer tube (20) may have any other suitable dimension.

As shown in FIGS. 3-4, a distal plug (70) is secured to the distal end of actuating rod (40). Distal plug (70) is thus translatable from a proximal position as shown in FIG. 3 to a distal position as shown in FIG. 4 by translating actuating rod (40) distally as described above. Distal plug (70) includes a resilient tab (72) that extends upwardly from distal plug (70). Resilient tab (72) is resiliently biased to extend upwardly from distal plug (70), but is movable downwardly toward distal plug (70) in order to allow distal plug (70) to fit within and translate within introducer tube (20). However, once distal plug (70) reaches the distal position shown in FIGS. 2 and 4, resilient tab (72) is configured to "snap into" side aperture (28) of introducer tube (20), such that at least a portion of resilient tab (72) protrudes into side aperture (28). With resilient tab (72) so engaged with side aperture (28), the longitudinal position of distal plug (70) may be substantially secured. In other words, engagement between resilient tab (72) and side aperture (28) may substantially prevent proximal movement of distal plug (70) once distal plug (70) has reached a distal position. Distal plug (70) may also include a recess below resilient tab (72), which may provide clearance for resilient tab (72) to deflect downwardly when distal plug (70) is proximal to the distal position shown in FIGS. 2 and 4. Such downward deflection on resilient tab (72) may be provided by the inner diameter of introducer tube (20) when distal plug (70) is proximal to the distal position shown in FIGS. 2 and 4.

One or more indentations (29) formed at distal end (26) of introducer tube (20) may also restrict distal positioning of distal plug (70). Such restriction of distal positioning of distal plug (70) may also restrict distal positioning of actuating rod (40). In addition or in the alternative, a feature on a proximal portion of actuating rod (40) may engage handle (22) when actuating rod (40) reaches a certain distal position, to arrest further distal translation of actuating rod (40) at a selected longitudinal position. In some such versions, distal plug (70) may even be omitted. For instance, resilient hoop member (80) may be integrally secured to actuating rod (40), such that a feature located near the proximal end of tissue retrieval device (10) that arrests distal translation of actuating rod (40) may effectively also arrest distal positioning of resilient hoop member (80).

As shown in FIGS. 2-4, a resilient hoop member (80) extends distally from distal plug (70). Resilient hoop member (80) is resiliently biased to assume an outwardly expanded circular or elliptical configuration as shown in FIGS. 2 and 4. However, resilient hoop member (80) has flexibility permitting resilient hoop member (80) to compress and deformably fit within introducer tube (20) as shown in FIGS. 1 and 3. A secure attachment between resilient hoop member (80) and distal plug (70) provides unitary translation of resilient hoop member (80) and distal plug (70) relative to introducer tube (20). In addition, a secure attachment between actuating rod (40) and distal plug (70) provides unitary translation of actuating rod (40) and distal plug (70). Thus, resilient hoop member (80) may be advanced from a proximal position as shown in FIG. 3 to a distal position as shown in FIG. 4 by advancing thumb ring (42) distally toward handle (22) as described above. Such distal advancement of resilient hoop member (80) moves resilient hoop member (80) from a proximal position where it is located within introducer tube (20) to a distal position where it protrudes from open distal end (26) of introducer tube (20).

Resilient hoop member (80) may be formed of any suitable material or combination of materials, including but not limited to metal (e.g., stainless steel, nitinol, steel spring alloys, copper spring alloys, etc.), plastic, and/or metal reinforced plastic. In addition, while resilient hoop member (80) is formed as a single unitary piece, resilient hoop member (80) may alternatively be formed of any other suitable number of pieces. By way of example only, resilient hoop member (80) may be formed of two separate arms that together provide a configuration that is substantially similar to the configuration shown for resilient hoop member (80), except that the two separate arms are separated at a region corresponding to the distal-most part of resilient hoop member (80). Other suitable variations of resilient hoop member (80) will be apparent to those of ordinary skill in the art in view of the teachings herein. By way of example only, resilient hoop member (80) may be readily substituted with any bag frame component or support structure disclosed in any of the patents or patent applications cited herein. Similarly, tissue retrieval device (10) may readily incorporate any of the various bag deployment mechanisms disclosed in any of the patents or patent applications cited herein. Various suitable ways in which such alternative bag frames, support structures, deployment mechanisms, and/or other teachings in any of the patents or patent applications cited herein may be incorporated into tissue retrieval device (10) will be apparent to those of ordinary skill in the art.

Retrieval bag (60) is secured to resilient hoop member (80) in the present example. For instance, resilient hoop member (80) may be fed through slits, one or more pockets, or one or more other features near the top opening of retrieval bag (60). The engagement between retrieval bag (60) and resilient hoop member (80) is such that retrieval bag (60) translates substantially unitarily with resilient hoop member (80) relative to introducer tube (20). Thus, retrieval bag (60) may be advanced from a proximal position as shown in FIGS. 1 and 3 to a distal position as shown in FIGS. 2 and 4 by advancing thumb ring (42) distally toward handle (22) as described above. In addition, the engagement between retrieval bag (60) and resilient hoop member (80) is such that resilient hoop member (80) substantially opens the top of retrieval bag (60) when resilient hoop member (80) reaches the expanded configuration shown in FIGS. 2 and 4. While resilient hoop member (80) is flexible enough to compressingly/compressibly fit within introducer tube (20), resilient hoop member (80) has sufficient rigidity to substantially support retrieval bag (60) when resilient hoop member (80) and retrieval bag (60) protrude from open distal end (26) of introducer tube (20).

Retrieval bag (60) may have any suitable configuration when retrieval bag (60) is positioned within introducer tube (20). For instance, retrieval bag (60) may be rolled up, folded up, wadded up, or have any other suitable configuration within introducer tube (20). When retrieval bag (60) has been advanced from a proximal position as shown in FIGS. 1 and 3 to a distal position as shown in FIGS. 2 and 4, a separate instrument (e.g., conventional tissue graspers, etc.) may be used to assist in unfurling retrieval bag (60). In addition or in the alternative, the material properties of retrieval bag (60) and/or gravity may cause retrieval bag (60) to at least substantially unfurl on its own once it has been deployed from introducer tube (20). With retrieval bag (60) deployed and opened as shown in FIGS. 2 and 4, a surgeon may place tissue samples or specimens, etc. (e.g., patient's gall bladder, etc.) within retrieval bag (60) for subsequent removal of such tissue samples or specimens, etc. from the patient.

In some versions, tissue retrieval device (10) may be configured such that retrieval bag (60) is removable from resilient hoop member (80) (e.g., while these components are still within the patient, etc.). Some such versions facilitate removal of retrieval bag (60) separate from removal of the other components of the tissue retrieval device (10) from the patient. For instance, in some versions tissue retrieval device (10) may include a closure string (not shown) connected to retrieval bag (60) and having a slipknot attachment to actuating rod (40). Pulling the slipknot loose from actuating rod (40) and then retracting actuating rod (40) proximally may permit detachment of retrieval bag (60) and the closure string from the other components of specimen retrieval device (10). For instance, actuating rod (40) may be fully withdrawn from introducer tube (20) and a free end of the closure string may protrude from the proximal end of introducer tube (20). In some such versions, a user may pull the closure string to close retrieval bag (60). For instance, the closure string may be engaged with retrieval bag (60) similar to a purse string. By way of example only, such a closure mechanism may be configured in accordance with the teachings of U.S. Pat. No. 6,409,733, entitled "Specimen Retrieval Bag," issued Jun. 25, 2002, the disclosure of which is incorporated by reference herein. In some such versions, retrieval bag (60) is perforated in a region between a closure string and the region where retrieval bag (60) is coupled with resilient hoop member (80). Such perforation may permit retrieval bag (60) to be separated from hoop member (80) without compromising engagement between the closure string and retrieval bag (60).

A closed retrieval bag (60) containing tissue may be removed through the same trocar through which introducer tube (20) was inserted. In particular, a closed retrieval bag (60) containing tissue may be removed through the trocar at the same time introducer tube (20) is removed from the trocar. Alternatively, introducer tube (20) may be removed from the trocar first, then the closed retrieval bag (60) containing tissue may be removed through the trocar. As yet another merely illustrative alternative, the closed retrieval bag (60) containing tissue may be removed from the patient after introducer tube (20) and the trocar have been removed from the patient. In other words, the closed retrieval bag (60) containing tissue may be removed directly through the incision through which the trocar had been previously inserted. In any of these scenarios, a protruding closure string may be used to remove retrieval bag (60) from the patient. Alternatively, retrieval bag (60) may be removed from the patient in any other suitable fashion.

In some versions, actuating rod (40) may comprise features operable with other features of introducer tube (20) or other components to prevent inadvertent retraction of actuating rod (40) during deployment of retrieval bag (60). For example, actuating rod (40) may include a one way ratcheting mechanism as described in U.S. Pat. No. 6,409,733, entitled "Specimen Retrieval Bag," issued Jun. 25, 2002, the disclosure of which is incorporated by reference herein. Other ways in which inadvertent retraction of actuating rod (40) may be avoided through various features of tissue retrieval device (10) will be apparent to those of ordinary skill in the art in view of the teachings herein.

In some alternative versions, tissue retrieval device (10) lacks actuating rod (40) altogether. In some such versions, the position of distal plug (70) in introducer tube (20) is substantially fixed. In addition, an external sheath (not shown) is slidably positioned about introducer tube (20). For instance, such an external sheath may be distally positioned to encompass resilient hoop member (80) and retrieval bag (60) as tissue retrieval device (10) is being inserted in a patient; then the external sheath may be proximally retracted relative to introducer tube (20) to expose resilient hoop member (80) and retrieval bag (60) within the patient. Such an external sheath may extend proximally enough to allow the external sheath to be externally manipulated by a surgeon. For instance, a proximal end of the external sheath may include a handle portion near handle (22) of introducer tube (20). Still other various suitable variations, components, features, configurations, and functionalities of tissue retrieval device (10) will be apparent to those of ordinary skill in the art in view of the teachings herein.

FIGS. 5-17 show various alternative tissue retrieval bags (100, 200, 300, 400, 500) that may be coupled with tissue retrieval device (10) or variations of tissue retrieval device. In particular, each of tissue retrieval bags (100, 200, 300, 400, 500) that may be secured to resilient hoop member (80) or some variation thereof or substitute therefor. Similarly, each of tissue retrieval bags (100, 200, 300, 400, 500) may be deployed from introducer tube (20) in a manner similar to retrieval bag (60) discussed above. Alternatively, any of tissue retrieval bags (100, 200, 300, 400, 500) may be readily coupled with any tissue retrieval device disclosed in any patent or patent application that is cited herein. Various suitable ways in which any of tissue retrieval bags (100, 200, 300, 400, 500) may be incorporated into such alternative tissue retrieval devices will be apparent to those of ordinary skill in the art in view of the teachings herein.

FIGS. 5-8 show a tissue retrieval bag (100) that is secured to a resilient hoop member (80) and that has an open end (102) and a closed end (104). Open end (102) provides an entry permitting the placement of material (130) (e.g., a tissue specimen, etc.) into retrieval bag (100). Retrieval bag (100) of the present example further comprises a plurality of folds (110) that provide retrieval bag (100) with a pleated or gusseted configuration. In the present example, folds (110) extend the full length of retrieval bag (100)—from open end (102) to closed end (104). Alternatively, folds (110) may extend along just a portion of the length of retrieval bag (100). For instance, folds (110) may begin at open end (102) of retrieval bag (100), extend downwardly, and stop short of closed end (104). Alternatively, folds (110) may begin at closed end (104), extend upwardly, and stop short of open end (102).

Figure 5:
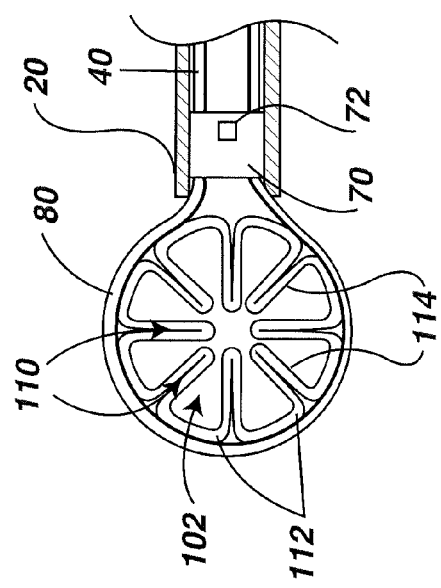
FIG. 5 is a top view of an exemplary alternative retrieval bag, in a deployed position and in an un-expanded configuration.
Figure 7:
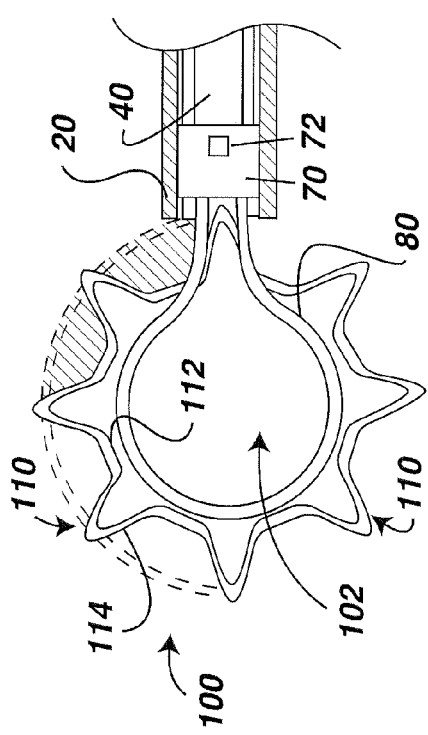
FIG. 7 is a top view of the retrieval bag of FIG. 5, in the deployed position and in an expanded configuration.

As best seen in FIGS. 5 and 7, some portions (112) at open end (102) of retrieval bag (100) are secured to resilient hoop member (80); while other portions (114) at open end (102) of retrieval bag (100) are not secured to resilient hoop member (80). In particular, folds (110) are formed by non-secured portions (114); and secured portions (112) are adjacent to folds (110). In some versions, secured portions (112) comprise pockets or features that are similar to belt loops on trousers, through which resilient hoop member (80) passes. For instance, the coupling between resilient hoop member (80) and secured portions (112) may permit secured portions (112) to rotate and/or slide about resilient hoop member (80).

Figure 6:
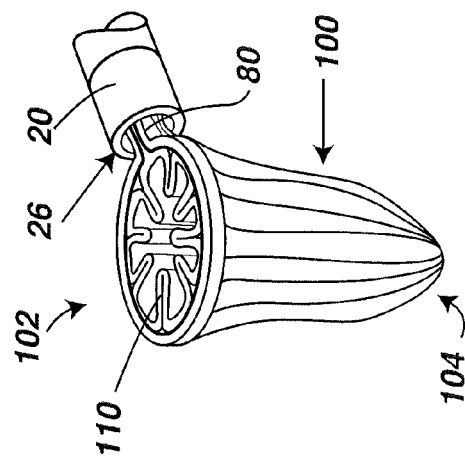
FIG. 6 is a perspective view of the retrieval bag of FIG. 5, in the deployed position and in the un-expanded configuration.
Figure 8:
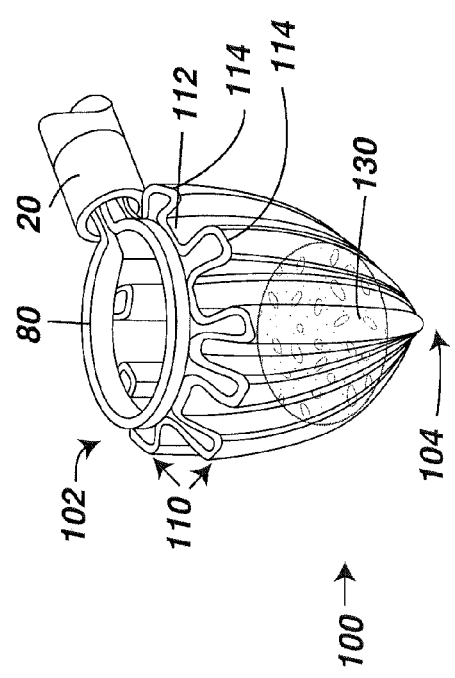
FIG. 8 is a perspective view of the retrieval bag of FIG. 5, in the deployed position and in the expanded configuration.

In other words, secured portions (112) may flexible move around resilient hoop member (80) in a folded manner, like a curtain on a curtain rod. As can be seen in FIGS. 6 and 8, such engagement permits the top edges of non-secured portions (114) to transition from a position that is near a plane defined by the top of resilient hoop member (80) to a position that is below a plane defined by the bottom of resilient hoop member (80). Alternatively, retrieval bag (100) may be secured to resilient hoop member (80) in any other suitable fashion. As can also be seen in FIGS. 5 and 7, folds (110) generally extend radially outwardly from a center point that lies along an axis that passes through the center of retrieval bag (100) and that passes through the center of the opening defined by resilient hoop member (80). It should be understood, however, that folds (110) may extend in any other suitable directions/planes.

As can be seen in FIGS. 5-8, folds (110) permit retrieval bag (100) to extend from an inverted or unexpanded configuration (FIGS. 5-6) to an everted or expanded configuration (FIGS. 7-8). Such expandability provided by folds (110) may thus provide an effective increase in the holding volume of retrieval bag (100). While retrieval bag (100) is disposed within introducer tube (20), retrieval bag (100) may be in the inverted or unexpanded configuration. Upon being initially deployed out through open distal end (26) of introducer tube (20), retrieval bag (100) may initially still be in the inverted or unexpanded configuration. However, retrieval bag (100) may ultimately transition to the everted or expanded configuration. By way of example only, gravity may cause retrieval bag (100) to transition from the inverted or unexpanded configuration to the everted or expanded configuration. In addition or in the alternative, the material forming retrieval bag (100) may be resiliently biased to transition retrieval bag (100) from the inverted or unexpanded configuration to the everted or expanded configuration. In addition or in the alternative, an additional instrument (e.g., conventional tissue graspers, etc.) may be used to assist in transitioning retrieval bag (100) from the inverted or unexpanded configuration to the everted or expanded configuration. As yet another merely illustrative example, placement of material (130) (e.g., a tissue specimen, etc.) in retrieval bag (100) may assist in transitioning retrieval bag (100) from the inverted or unexpanded configuration to the everted or expanded configuration. Still other suitable ways in which retrieval bag (100) may be transitioned from an inverted or unexpanded configuration to an everted or expanded configuration will be apparent to those of ordinary skill in the art in view of the teachings herein.

Retrieval bag (100) may be initially retracted within introducer tube (20), much like the configurations shown in FIGS. 1 and 5. Introducer tube (20) may then be inserted into a patient (e.g., via a trocar, natural orifice, incision, etc.). Retrieval bag (100) may then be advanced to a distal position as shown in FIGS. 5-6. Such distal advancement of retrieval bag (100) may be accomplished in accordance with any of the explicit teachings herein or using any suitable components, structures, features, or techniques that may be apparent to one of ordinary skill in the art in view of the teachings herein. By way of example only, an actuation rod (40) may be advanced distally relative to introducer tube (20) to distally expose retrieval bag (100) relative to introducer tube (20). As another merely illustrative example, a sheath about introducer tube (20) may be retracted proximally relative to introducer tube (20) to reveal retrieval bag (100). The resilience of resilient hoop member (80) may place retrieval bag (100) in the deployed position shown in FIGS. 5-6. Retrieval bag (100) may then be transitioned to an everted or expanded configuration as shown in FIGS. 7-8 and as described above.

With retrieval bag (100) in the open and expanded position as shown in FIGS. 7-8, material (130) may be placed in open end (102) of retrieval bag (100). Retrieval bag (100) may then be closed to substantially contain material (130) within retrieval bag (100). By way of example only, retrieval bag (100) may incorporate a closure string as described above, a belt, a cable tie, or some other cinching feature to close retrieval bag (100). Other suitable ways in which retrieval bag (100) may be closed will be apparent to those of ordinary skill in the art in view of the teachings herein. Once retrieval bag (100) has been sufficiently closed, retrieval bag (100) may be removed from the patient in accordance with any of the above teachings relating to the removal of a closed retrieval bag (60) containing tissue. Alternatively, retrieval bag (100) may be removed from the patient in any other suitable fashion.

FIGS. 9-10 show another exemplary tissue retrieval bag (200). In this example, resilient hoop (80) is substituted with telescoping hoop (280), which will be described in greater detail below. Tissue retrieval bag (200) is secured to telescoping hoop (280), and has an open end (202) and a closed end (204). Open end (202) provides an entry permitting the placement of material (e.g., a tissue specimen, etc.) into retrieval bag (200). Retrieval bag (200) of the present example further comprises a plurality of folds (210) that provide retrieval bag (200) with a pleated or gusseted configuration. In the present example, folds (210) extend the full length of retrieval bag (200)—from open end (202) to closed end (204). Alternatively, folds (210) may extend along just a portion of the length of retrieval bag (200). For instance, folds (210) may begin at open end (202) of retrieval bag (200), extend downwardly, and stop short of closed end (204).

Like resilient hoop member (80), telescoping hoop (80) is retractable within introducer tube (20), and may be translated within introducer tube (20) from a proximal position in which telescoping hoop (80) is contained within introducer tube (20) to a distal position in which telescoping hoop (80) protrudes from distal end (26) of introducer tube (20). By way of example only, telescoping hoop (280) may be secured to distal plug (70), to the distal end of actuating rod (40), or to any other suitable structure. In some versions, the longitudinal position of telescoping hoop (280) relative to introducer tube (20) is substantially fixed. For instance, a retractable sheath (not shown) may be positioned about telescoping hoop (280) to substantially contain telescoping hoop (280) and retrieval bag (200). Such a retractable sheath may be retracted to reveal telescoping hoop (280) and retrieval bag (200), allowing telescoping hoop (280) to expand from a collapsed configuration to an expanded or partially expanded configuration.

Telescoping hoop (280) of the present example comprises a plurality of segments (282) that are telescopingly coupled together, and that are slidable relative to each other to expand the diameter defined by telescoping hoop (280). In particular, segments (282) are shown in a first position in FIG. 9 where telescoping hoop (280) forms a relatively smaller diameter; while segments (282) are shown in a second position in FIG. 10 where telescoping hoop (280) forms a relatively larger diameter. In the present example, telescoping hoop (280) is still compressible to fit within the interior of introducer tube (20) when retrieval bag (200) is retracted to a proximal position within introducer tube (20). In some versions, segments (282) are resiliently biased to separate from each other to provide the expanded diameter shown in FIG. 10. For instance, spring members may be positioned within and between adjacent segments (282). In some such versions, telescoping hoop (280) automatically transitions from the contracted configuration shown in FIG. 9 to the expanded configuration shown in FIG. 10 after telescoping hoop (280) is exposed relative to introducer tube (20). In some other versions, one or more actuators are used to transition telescoping hoop (280) from the contracted configuration shown in FIG. 9 to the expanded configuration shown in FIG. 10. Such actuators may require a separate activation by the user to transition telescoping hoop (280) from the contracted configuration shown in FIG. 9 to the expanded configuration shown in FIG. 10 after telescoping hoop (280) is exposed relative to introducer tube (20). Still other suitable ways in which telescoping hoop (280) may be transitioned from the contracted configuration shown in FIG. 9 to the expanded configuration shown in FIG. 10 will be apparent to those of ordinary skill in the art in view of the teachings herein.

Some portions (212) at open end (202) of retrieval bag (200) are secured to telescoping hoop (280), while other portions (214) at open end (102) are not secured to telescoping hoop (280). In particular, folds (210) are formed by non-secured portions (214) and secured portions (212), which are adjacent to folds (210), in an alternating and circumferential manner. In some versions, each secured portion (212) of retrieval bag (200) is fixedly secured to a corresponding segment (282) of telescoping hoop (280), such that each secured portion (212) of retrieval bag (200) moves substantially unitarily with its corresponding segment (282) of telescoping hoop (280). Accordingly, when telescoping hoop (280) transitions from the contracted configuration shown in FIG. 9 to the expanded configuration shown in FIG. 10, open end (202) of retrieval bag (200) also expands from a contracted configuration to an expanded configuration. In other words, the effective diameter of open end (202) of retrieval bag (200) is increased. Such an increase in the effective diameter of open end (202) of retrieval bag (200) is permitted or facilitated in part by the presence of folds (210) and non-secured portions (214). Furthermore, such expansion of retrieval bag (200) may increase the effective holding volume of retrieval bag (200).

Retrieval bag (200) may be initially retracted within introducer tube (20), much like the configurations shown in FIGS. 1 and 5. Introducer tube (20) may then be inserted into a patient (e.g., via a trocar, natural orifice, incision, etc.). Retrieval bag (200) may then be advanced to a distal position as shown in FIGS. 5-6. Such distal advancement of retrieval bag (200) may be accomplished in accordance with any of the explicit teachings herein or using any suitable components, structures, features, or techniques that may be apparent to one of ordinary skill in the art in view of the teachings herein. By way of example only, an actuation rod (40) may be advanced distally relative to introducer tube (20) to distally expose retrieval bag (200) relative to introducer tube (20). As another merely illustrative example, a sheath about introducer tube (20) may be retracted proximally relative to introducer tube (20) to reveal retrieval bag (200). The resilience of telescoping hoop (280) may initially place retrieval bag (200) in the deployed position shown in FIG. 9. Movement by segments (282) may then transition retrieval bag (200) to an expanded configuration as shown in FIG. 10 and as described above.

With retrieval bag (200) in the open and expanded position as shown in FIG. 10, material (e.g., a tissue specimen, etc.) may be placed in open end (202) of retrieval bag (200). Retrieval bag (200) may then be closed to substantially contain the material within retrieval bag (200). Segments (282) may retract relative to each other to place telescoping hoop (280) back in the contracted configuration shown in FIG. 9 as part of this closure process. In addition, retrieval bag (200) may incorporate a closure string as described above, a belt, a cable tie, or some other cinching feature to close retrieval bag (100). Other suitable ways in which retrieval bag (200) may be closed will be apparent to those of ordinary skill in the art in view of the teachings herein. Once retrieval bag (200) has been sufficiently closed, retrieval bag (200) may be removed from the patient in accordance with any of the above teachings relating to the removal of a closed retrieval bag (60) containing tissue. Alternatively, retrieval bag (200) may be removed from the patient in any other suitable fashion.

FIGS. 11-12 show another exemplary tissue retrieval bag (300). In this example, resilient hoop (80) is substituted with a pair of arms (380). In particular, arms (380) are pre-curved and are resiliently biased to expand outwardly relative to each other yet maintain an orientation such that arms (380) are substantially parallel to each other and to introducer tube (20). Arms (380) may nevertheless be deformed to fit within introducer tube (20), such as when arms (380) and retrieval bag (300) are retracted proximally within introducer tube (20). Arms (380) may be formed of any suitable material or combination of materials, including but not limited to metal (e.g., stainless steel, nitinol, steel spring alloys, copper spring alloys, etc.), plastic, and/or metal reinforced plastic. By way of example only, arms (380) may be secured to distal plug (70), to the distal end of actuating rod (40), or to any other suitable structure. In some versions, the longitudinal position of arms (380) relative to introducer tube (20) is substantially fixed. For instance, a retractable sheath (not shown) may be positioned about arms (380) to substantially contain arms (380) and retrieval bag (300). Such a retractable sheath may be retracted to reveal arms (380) and retrieval bag (300), allowing arms (380) to expand from a collapsed configuration to an expanded or partially expanded configuration. In an expanded configuration, arms (380) form a "Y" shape in the present example. Alternatively, expanded arms (380) may form a "U" shape, a "V" shape, or any other suitable shape.

Retrieval bag (300) of the present example is secured to arms (380), and has an open end (302) and a closed end (304). Open end (302) provides an entry permitting the placement of material (e.g., a tissue specimen, etc.) into retrieval bag (300). A plurality of tabs (306) extend upwardly from open end (302) of retrieval bag (300) to secure retrieval bag (300) to arms (380). Loops (308) are formed at the top ends of tabs (306), and arms (380) are inserted through loops (308). Loops (308) may be further secured to arms (380) by adhesives or using any other suitable substances, features, devices, or techniques. Retrieval bag (300) of the present example further comprises a plurality of folds (310). Folds (310) are formed in closed end (304) of retrieval bag (300), and extend in a longitudinal direction. In particular, folds (310) extend in a direction that is parallel to the longitudinal axis defined by introducer tube (20). Alternatively, folds (310) may extend along any other suitable direction.

In the present example, folds (310) permit closed end (304) of retrieval bag (300) to be neatly folded up such that most of the lower portion of a retrieval bag (300) is positioned within open end (302) of retrieval bag (302) when retrieval bag (300) is in a folded configuration as shown in FIG. 11. With retrieval bag (300) in such a folded configuration, retrieval bag (300) may fit within introducer tube (20) and may move from a proximal position in which retrieval bag (300) is located within introducer tube (20) to a distal position as shown in FIGS. 11-12. When folded and positioned within introducer tube (20), retrieval bag (300) may be positioned between arms (380). In addition or in the alternative, when folded and positioned within introducer tube (20), retrieval bag (300) may be positioned between the lower portions of arms (380) and the inner diameter of introducer tube (20). In addition, as shown in FIG. 11, tabs (306) may also be folded when retrieval bag (300) is in a folded configuration. Of course, retrieval bag (300) may be folded in any other suitable fashion. Furthermore, a folded retrieval bag (300) may have any other suitable positioning and configuration relative to arms (380) when arms (380) and retrieval bag (300) are retracted to a proximal position within introducer tube (20). Other suitable positions and folding configurations for retrieval bag (300) will be apparent to those of ordinary skill in the art in view of the teachings herein. It should be understood that retrieval bag (300) may expand at folds (310) to substantially increase the effective holding volume of retrieval bag (300).

Retrieval bag (300) may be initially retracted within introducer tube (20), much like the configurations shown in FIGS. 1 and 5. Introducer tube (20) may then be inserted into a patient (e.g., via a trocar, natural orifice, incision, etc.). Retrieval bag (300) may then be advanced to a distal position as shown in FIGS. 11-12. Such distal advancement of retrieval bag (300) may be accomplished in accordance with any of the explicit teachings herein or using any suitable components, structures, features, or techniques that may be apparent to one of ordinary skill in the art in view of the teachings herein. By way of example only, an actuation rod (40) may be advanced distally relative to introducer tube (20) to distally expose retrieval bag (300) relative to introducer tube (20). As another merely illustrative example, a sheath about introducer tube (20) may be retracted proximally relative to introducer tube (20) to reveal retrieval bag (300). The resilience of arms (380) may urge arms (380) apart, which may in turn open the open end (302) of retrieval bag (300). Retrieval bag (300) may then unfold from the folded configuration shown in FIG. 11 to the unfolded configuration shown in FIG. 12. By way of example only, such unfolding may be provided or facilitated by gravity, a resiliency in material forming retrieval bag (300), use of a separate instrument (e.g., conventional tissue graspers, etc.), placement of material (e.g., a tissue specimen, etc.) in retrieval bag (300), or in any other suitable fashion.

With retrieval bag (300) in the open and expanded position as shown in FIG. 12, material (e.g., a tissue specimen, etc.) may be placed in open end (302) of retrieval bag (300). Retrieval bag (300) may then be closed to substantially contain the material within retrieval bag (300). By way of example only, retrieval bag (300) may incorporate a closure string as described above, a belt, a cable tie, or some other cinching feature to close retrieval bag (300). Other suitable ways in which retrieval bag (300) may be closed will be apparent to those of ordinary skill in the art in view of the teachings herein. Once retrieval bag (300) has been sufficiently closed, retrieval bag (300) may be removed from the patient in accordance with any of the above teachings relating to the removal of a closed retrieval bag (60) containing tissue. Alternatively, retrieval bag (300) may be removed from the patient in any other suitable fashion.

FIGS. 13-14 show yet another exemplary tissue retrieval bag (400). Retrieval bag (400) of this example is secured to a resilient hoop member (80) and has an open end (402) and a closed end (404). Open end (402) provides an entry permitting the placement of material (e.g., a tissue specimen, etc.) into retrieval bag (400). Retrieval bag (400) of the present example has a substantially cylindraceous shape, though it should be understood that retrieval bag (400) may alternatively have any other suitable shape. Retrieval bag (400) of the present example further comprises a plurality of circumferential folds (410) that provide retrieval bag (400) with a longitudinally collapsible, bellows-type configuration. In the present example, folds (410) each extend about the full circumference of retrieval bag (400), and are positioned along the full length of retrieval bag (400)—from open end (402) to closed end (404). Alternatively, folds (410) may be positioned along just a portion of the length of retrieval bag (400). For instance, folds (410) may begin at open end (402) of retrieval bag (400) and only be positioned along a top part of the length of retrieval bag (400). Alternatively, folds (410) may begin at closed end (104) and only be positioned along a bottom part of the length of retrieval bag (400).

Resilient hoop member (80) may extend through one or more pockets, slits, slots, or other features at open end of retrieval bag (400). As noted above, resilient hoop member (80) may be collapsible to fit within introducer tube (20) when resilient hoop member (80) is at a proximal position, yet may still resiliently expand to the configuration shown in FIGS. 13-14 when resilient hoop member (80) is exposed. In addition, retrieval bag (400) may collapse further to fit within introducer tube (20) when resilient hoop member (80) is at a proximal position. When resilient hoop member (80) and retrieval bag (400) initially exposed, retrieval bag (400) may have the collapsed configuration shown in FIG. 13, where closed end (404) is substantially close to open end (402). Such a collapsed configuration may be facilitated in part by folds (410). However, retrieval bag (400) may then reach the expanded configuration shown in FIG. 14, where closed end (404) is substantially further from open end (402). Retrieval bag (400) may thus expand at folds (410) to substantially increase the effective holding volume of retrieval bag (400).

Retrieval bag (400) may be initially retracted within introducer tube (20), much like the configurations shown in FIGS. 1 and 5. Introducer tube (20) may then be inserted into a patient (e.g., via a trocar, natural orifice, incision, etc.). Retrieval bag (400) may then be advanced to a distal position as shown in FIGS. 13-14. Such distal advancement of retrieval bag (400) may be accomplished in accordance with any of the explicit teachings herein or using any suitable components, structures, features, or techniques that may be apparent to one of ordinary skill in the art in view of the teachings herein. By way of example only, an actuation rod (40) may be advanced distally relative to introducer tube (20) to distally expose retrieval bag (400) relative to introducer tube (20). As another merely illustrative example, a sheath about introducer tube (20) may be retracted proximally relative to introducer tube (20) to reveal retrieval bag (400). The resilience of resilient hoop member (80) may place retrieval bag (400) in the deployed position shown in FIGS. 13-14. Retrieval bag (400) may then expand from the collapsed configuration shown in FIG. 13 to the expanded configuration shown in FIG. 14. By way of example only, such expansion may be provided or facilitated by gravity, a resiliency in material forming retrieval bag (400), use of a separate instrument (e.g., conventional tissue graspers, etc.), placement of material (e.g., a tissue specimen, etc.) in retrieval bag (400), or in any other suitable fashion.

With retrieval bag (400) in the open and expanded position as shown in FIG. 14, material (e.g., a tissue specimen, etc.) may be placed in open end (402) of retrieval bag (400). Retrieval bag (400) may then be closed to substantially contain the material within retrieval bag (400). By way of example only, retrieval bag (400) may incorporate a closure string as described above, a belt, a cable tie, or some other cinching feature to close retrieval bag (400). Other suitable ways in which retrieval bag (400) may be closed will be apparent to those of ordinary skill in the art in view of the teachings herein. Once retrieval bag (400) has been sufficiently closed, retrieval bag (400) may be removed from the patient in accordance with any of the above teachings relating to the removal of a closed retrieval bag (60) containing tissue.

Alternatively, retrieval bag (400) may be removed from the patient in any other suitable fashion.

Figure 15:
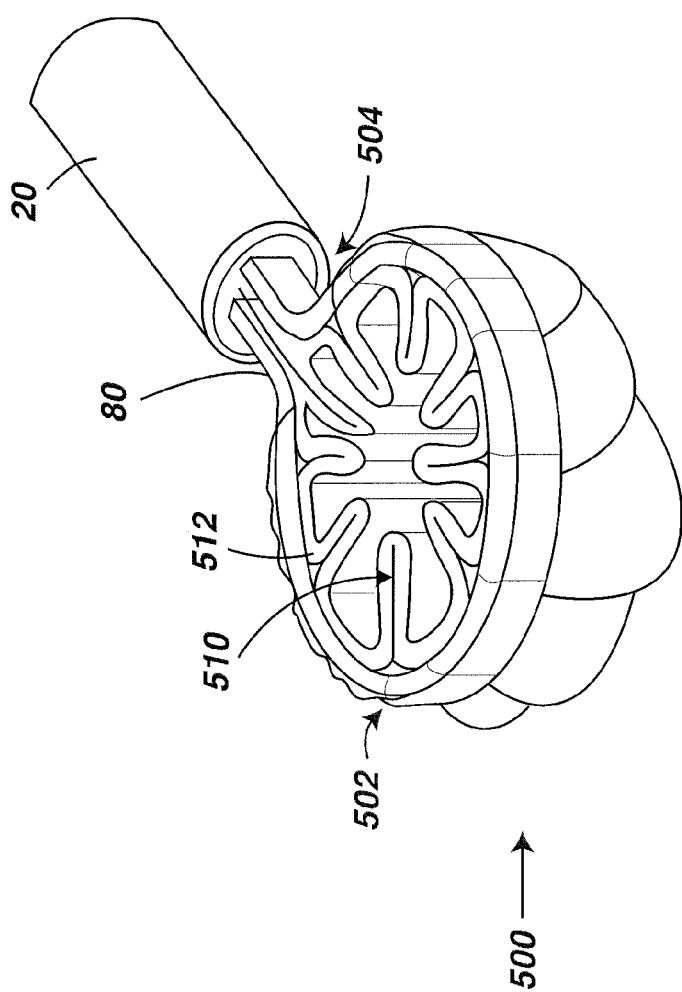
FIG. 15 is a perspective view of another exemplary alternative retrieval bag, in a partially deployed position and in an un-expanded configuration.
Figure 16:
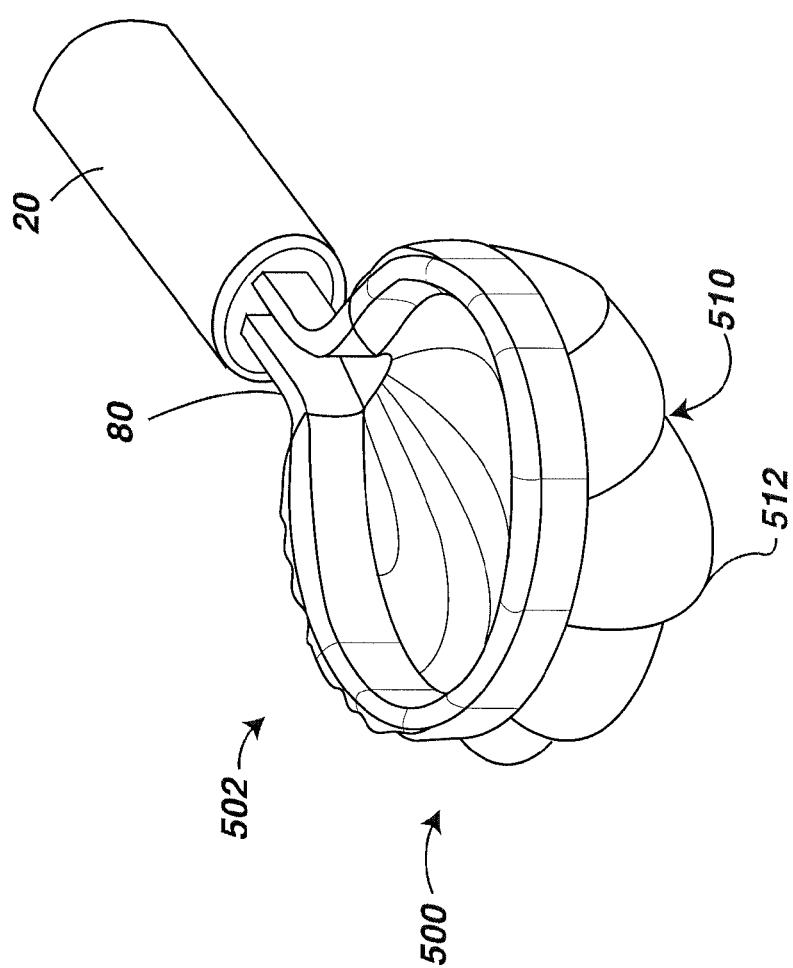
FIG. 16 is a perspective view of the retrieval bag of FIG. 15, in a fully deployed position and in a partially expanded configuration.

FIGS. 15-17 show another exemplary tissue retrieval bag (500). Retrieval bag (500) of this example is secured to a resilient hoop member (80) and has an open end (502) and a closed end (504). Open end (502) provides an entry permitting the placement of material (e.g., a tissue specimen, etc.) into retrieval bag (500). Retrieval bag (500) of the present example comprises a plurality of petals (512) that provide retrieval bag (500) with a beach ball like configuration. In particular, each petal (512) is formed by opposing sides that have a substantially elliptical curvature. Such elliptical sides of adjacent petals (512) are secured to each other. Thus, the shape and arrangement of petals (512) provides retrieval bag (500) with a substantially spherical configuration when retrieval bag (500) is fully expanded as shown in FIG. 17. It should be understood, however, that petals (512) may have any other suitable shape and arrangement; and that a fully expanded retrieval bag (500) may have any other suitable shape.

FIG. 15 shows resilient hoop member (80) only partially extended/deployed from introducer tube (20). In this configuration, closed end (504) remains within introducer tube (20). In addition, petals (512) form folds (510) that are directed in a radial direction relative to an axis extending through a center point defined by resilient hoop member (80) in this configuration. FIG. 16 shows resilient hoop member (80) fully extended/deployed from introducer tube (20). In this configuration, retrieval bag (500) is not yet fully expanded. In FIG. 17, retrieval bag (500) is in a fully expanded configuration, containing material (530) (e.g., tissue specimen, etc.) obtained from the patient's body. Retrieval bag (500) may thus expand at folds (510) to substantially increase the effective holding volume of retrieval bag (500).

Retrieval bag (500) may be initially retracted within introducer tube (20), much like the configurations shown in FIGS. 1 and 5. Introducer tube (20) may then be inserted into a patient (e.g., via a trocar, natural orifice, incision, etc.). Retrieval bag (500) may then be advanced to a distal position as shown in FIGS. 16-17. Such distal advancement of retrieval bag (500) may be accomplished in accordance with any of the explicit teachings herein or using any suitable components, structures, features, or techniques that may be apparent to one of ordinary skill in the art in view of the teachings herein. By way of example only, an actuation rod (40) may be advanced distally relative to introducer tube (20) to distally expose retrieval bag (500) relative to introducer tube (20). As another merely illustrative example, a sheath about introducer tube (20) may be retracted proximally relative to introducer tube (20) to reveal retrieval bag (500). The resilience of resilient hoop member (80) may place retrieval bag (500) in the deployed position shown in FIGS. 16-17. Retrieval bag (500) may then expand from the collapsed configuration shown in FIGS. 15-16 to the expanded configuration shown in FIG. 17. By way of example only, such expansion may be provided or facilitated by gravity, a resiliency in material forming retrieval bag (500), use of a separate instrument (e.g., conventional tissue graspers, etc.), placement of material (e.g., a tissue specimen, etc.) in retrieval bag (500), or in any other suitable fashion.

With retrieval bag (500) in the open and expanded position as shown in FIG. 17, material (530) (e.g., a tissue specimen, etc.) may be placed in open end (502) of retrieval bag (500). Retrieval bag (500) may then be closed to substantially contain the material within retrieval bag (500). By way of example only, retrieval bag (500) may incorporate a closure string as described above, a belt, a cable tie, or some other cinching feature to close retrieval bag (500). Other suitable ways in which retrieval bag (500) may be closed will be apparent to those of ordinary skill in the art in view of the teachings herein. Once retrieval bag (500) has been sufficiently closed, retrieval bag (500) may be removed from the patient in accordance with any of the above teachings relating to the removal of a closed retrieval bag (60) containing tissue. Alternatively, retrieval bag (500) may be removed from the patient in any other suitable fashion.

It should be understood that the components, features, and configurations of tissue retrieval devices shown in FIGS. 1-17 are merely exemplary. As one merely illustrative alternative, a tissue retrieval device, tissue retrieval bag, and/or related components/features may be configured in accordance with the teachings of U.S. patent application Ser. No. 12/692,670, entitled "Tissue Retrieval Device with Modular Pouch Cartridge," filed filed Jan. 25, 2010, the disclosure of which is incorporated by reference herein. As another merely illustrative example, a tissue retrieval device, tissue retrieval bag, and/or related components/features may be configured in accordance with the teachings of U.S. patent application Ser. No. 12/693,476, entitled "Tissue Retrieval Device with Pouch Stretching Arm," filed Jan. 26, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,709, entitled "Tissue Retrieval Device with Buckling Arms," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,733, entitled "Tissue Retrieval Device with Bladders," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,727, entitled "Tissue Retrieval Device with Resilient Member," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/693,485, entitled "Method of Fitting Pouch in Tissue Retrieval Device," filed Jan. 26, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/693,498, entitled "Tissue Retrieval Device with Reinforced Pouch and Variable Volume," filed Jan. 26, 2010, the disclosure of which is incorporated by reference herein. Furthermore, various ways in which the teachings herein may be combined with the teachings of any of the above-referenced patent applications will be apparent to those of ordinary skill in the art.

Still other suitable components, features, configurations, and operabilities that may be provided by a tissue retrieval device and/or tissue retrieval bag, etc. will be apparent to those of ordinary skill in the art in view of the teachings herein.

It should be understood that any feature(s) and/or operability described herein with respect to one particular retrieval bag (60, 100, 200, 300, 400, 500) may be incorporated into any other retrieval bag (60, 100, 200, 300, 400, 500) described herein. Therefore, none of the teachings herein should be understood as being applicable to only one particular version or embodiment of retrieval bag (60, 100, 200, 300, 400, 500) described herein. Every teaching herein is contemplated as being interchangeable among versions and embodiments, such that every teaching herein may be applied to any retrieval bag (60, 100, 200, 300, 400, 500) described herein. Various ways in which the teachings herein may be interchanged among various versions and embodiments will be apparent to those of ordinary skill in the art in view of the teachings herein.

As noted above, the various versions of retrieval device (10) described herein, including but not limited to the various versions of retrieval bag (60, 100, 200, 300, 400, 500) described herein, may be used in a conventional endoscopic procedure that includes the insertion of the introducer tube (20) or other component through a small opening, e.g., an incision, natural orifice, or trocar access port. Of course, retrieval device (10) may be used in conjunction with any other suitable surgical or medical procedure, such as endoscopic/laparoscopic procedures, open surgical procedures, or robotic-assisted surgery, etc. Still other various settings and combinations in which a retrieval device (10) or retrieval bag (60, 100, 200, 300, 400, 500) may be used will be apparent to those of ordinary skill in the art in view of the teachings herein.

While several retrieval bags and deployment mechanisms have been discussed in detail above, it should be understood that the components, features, configurations, and methods of using the bags and deployment mechanisms discussed are not limited to the contexts provided above. In particular, components, features, configurations, and methods of use described in the context of one of the retrieval bags may be incorporated into any of the other retrieval bags. One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed. Still other additional and alternative suitable components, features, configurations, and methods of using the above-described retrieval devices will be apparent to those of ordinary skill in the art in view of the teachings herein.

While several tissue retrieval instruments and components thereof have been discussed in detail above, it should be understood that the components, features, configurations, and methods of using the tissue retrieval instruments discussed are not limited to the contexts provided above. In particular, components, features, configurations, and methods of use described in the context of one of the tissue retrieval instruments may be incorporated into any of the other tissue retrieval instruments. One merely exemplary additional feature that may be provided in any of the tissue retrieval instruments described herein includes retrieval bags having various sizes and geometries. For example, some tissue retrieval instruments may be designed with small, medium, or large retrieval bags. It should also be understood that any of the tissue retrieval instruments and tissue retrieval bags described herein may be capable of receiving tissue specimens and removing tissue specimens from a patient without such tissue specimens needing to be morcellated or otherwise reduced in size before being received and removed by the tissue retrieval instrument and bag. Still other additional and alternative suitable components, features, configurations, and methods of using the tissue retrieval instruments will be apparent to those of ordinary skill in the art in view of the teachings herein.

While the tissue retrieval instruments of the above-described examples are actuated manually by advancing a thumb ring distally relative to finger rings, by manually retracting a sheath, or in some other manual fashion, it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethyelene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient. In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted. Other suitable variations of a tissue retrieval bag will be apparent to those of ordinary skill in the art in view of the teachings herein.

Versions of the present invention have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical instrument for removal of material from a patient, the surgical instrument comprising:
   a. a handle assembly;
   b. an introducer tube, wherein the introducer tube is sized for insertion through a trocar, wherein the introducer tube comprises a proximal end and a distal end, wherein the proximal end of the introducer tube is in communication with the handle assembly; and
   c. a retrieval bag, wherein the retrieval bag is positionable at the distal end of the introducer tube, wherein the retrieval bag has an open end and a closed end, wherein the open end is configured to transition between a first open position and a second closed position, wherein the retrieval bag defines a bag length extending from the open end to the closed end, the retrieval bag further comprising a plurality of folds extending along at least part of the bag length when the open end is in the first open position and when the open end is in the second closed position, wherein the plurality of folds are comprised of a resilient material and are configured to provide the retrieval bag with an inverted configuration and an everted configuration, the everted configuration providing a volume capacity in the retrieval bag that is greater than a volume capacity of the bag in the inverted configuration.

2. The surgical instrument of claim 1, further comprising a resilient frame coupling retrieval bag with the introducer tube, wherein at least part of the open end of the retrieval bag is secured to the resilient frame.

3. The surgical instrument of claim 2, wherein the open end of the retrieval bag comprises a plurality of portions that are intermittently attached to the resilient frame and a plurality of portions that are not attached to the resilient frame.

4. The surgical instrument of claim 3, wherein the plurality of portions that are intermittently attached to the resilient frame form the plurality of folds.

5. The surgical instrument of claim 3, wherein the resilient frame has a top portion and a bottom portion, wherein the bottom portion of the resilient frame defines a plane, wherein the portions of the retrieval bag that are not attached to the resilient frame terminate below the plane defined by the bottom portion of the resilient frame.

6. The surgical instrument of claim 2, wherein the resilient frame is resiliently biased to assume a generally circular configuration.

7. The surgical instrument of claim 2, wherein the resilient frame and the retrieval bag are translatable relative to the introducer tube.

8. The surgical instrument of claim 7, wherein the resilient frame and the retrieval bag are translatable from a proximal position to a distal position, wherein the resilient frame and the retrieval bag are positioned within the introducer tube when the resilient frame and the retrieval bag are at the proximal position, wherein the resilient frame and the retrieval bag are exposed relative to the introducer tube when the resilient frame and the retrieval bag are in the distal position.

9. The surgical instrument of claim 7, further comprising an actuating rod secured to the resilient frame, wherein the actuating rod is movable relative to the introducer tube to translate the resilient frame and the retrieval bag relative to the introducer tube.

10. The surgical instrument of claim 9, wherein the actuating rod has a distal end and a proximal end, wherein the introducer tube has a distal end and a proximal end, wherein the resilient frame is secured to the distal end of the actuating rod, wherein the proximal end of the actuating rod is positioned proximal to the proximal end of the introducer tube.

11. The surgical instrument of claim 2, wherein the plurality of folds extend along the entirety of the bag length.

12. The surgical instrument of claim 1, wherein the plurality of folds are configured to provide the retrieval bag with an inverted configuration and an everted configuration, the everted configuration providing a volume capacity in the retrieval bag that is greater than a volume capacity of the bag in the inverted configuration.

13. A surgical instrument for removal of material from a patient, the surgical instrument comprising:
   a. a handle assembly;
   b. an introducer tube, wherein the introducer tube is sized for insertion through a trocar, wherein the introducer tube comprises a proximal end and a distal end, wherein the proximal end of the introducer tube is in communication with the handle assembly;

c. a retrieval bag, wherein the retrieval bag is positionable at the distal end of the introducer tube, wherein the retrieval bag has an open end and a closed end, wherein the retrieval bag defines a bag length extending from the open end to the closed end, the retrieval bag further comprising a plurality of folds extending along at least part of the bag length; and d. a resilient frame coupling the retrieval bag with the introducer tube, wherein at least part of the open end of the retrieval bag is secured to the resilient frame, wherein the open end of the retrieval bag comprises a plurality of portions that are intermittently attached to the resilient frame and a plurality of portions that are not attached to the resilient frame, wherein the plurality of folds are comprised of a resilient material and are configured to provide the retrieval bag with an inverted configuration and an everted configuration, the everted configuration providing a volume capacity in the retrieval bag that is greater than a volume capacity of the bag in the inverted configuration.

14. A surgical instrument for removal of material from a patient, the surgical instrument comprising:

a. a handle assembly;

b. an introducer tube, wherein the introducer tube is sized for insertion through a trocar, wherein the introducer tube comprises a proximal end and a distal end, wherein the proximal end of the introducer tube is in communication with the handle assembly; and c. a retrieval bag, wherein the retrieval bag is positionable at the distal end of the introducer tube, wherein the retrieval bag has an open end and a closed end, wherein the open end is configured to transition between a first open position and a second closed position, wherein the retrieval bag defines a bag length extending from the open end to the closed end, the retrieval bag further comprising a plurality of folds extending along at least part of the bag length; and d. a resilient frame coupling the retrieval bag with the introducer tube, wherein at least part of the open end of the retrieval bag is secured to the resilient frame;

wherein the plurality of folds are comprised of a resilient material and are configured to provide the retrieval bag with an inverted configuration and an everted configuration, the everted configuration providing a volume capacity in the retrieval bag that is greater than a volume capacity of the bag in the inverted configuration.

15. The surgical instrument of claim 14, wherein the open end of the retrieval bag comprises a plurality of portions that are intermittently attached to the resilient frame and a plurality of portions that are not attached to the resilient frame, wherein the plurality of portions that are not attached to the resilient frame laterally extend from the resilient frame, wherein each portion of the plurality of portions that are not attached to the resilient frame comprises a fold from the plurality of folds when the open end of the bag is in the first open position or when the open end of the bag is in the second closed position.

* * * * *